United States Patent [19]
Ozawa et al.

[11] Patent Number: 5,740,223
[45] Date of Patent: Apr. 14, 1998

[54] FLUORESCENT X-RAY ANALYZER WITH SEALED X-RAY SHIELD WALL

[75] Inventors: Sumito Ozawa; Yoshinori Hosokawa; Kozo Kashihara; Gensiro Setou, all of Miyanohigashi-machi, Japan

[73] Assignee: Horiba, Ltd., Kyoto, Japan

[21] Appl. No.: 759,371

[22] Filed: Dec. 4, 1996

[51] Int. Cl.$^6$ .................................................. G21K 1/04
[52] U.S. Cl. .................................... 378/161; 378/44
[58] Field of Search ............................. 378/161, 44

[56] References Cited

U.S. PATENT DOCUMENTS 3,889,113  6/1975  Rhodes ............................ 250/272

FOREIGN PATENT DOCUMENTS 4130556  9/1991  Germany.
2191285  9/1987  United Kingdom ............ 378/44

OTHER PUBLICATIONS

"Energy-dispersive x-ray spectrometry for multielement pollution analysis", by J.R. Rhodes, International Laboratory, Jul./Aug. 1973.

*Primary Examiner*—Don Wong
*Attorney, Agent, or Firm*—Price, Gess & Ubell

[57] ABSTRACT

A X-ray analyzer can generate an X-ray beam for application to a sample position during a support sample stage. An X-ray shield wall having an aperture transmissive to the X-ray beams is positioned adjacent to the supporting sample stage with a transparent film member sealingly extending across the aperture. An X-ray detector is positioned adjacent the X-ray shield wall. The upper side of the X-ray shield wall can be sealed and placed in a vacuum state or backfilled with a gas such as helium. The sample can be mounted at atmospheric pressure beneath the aperture and X-ray shield wall whereby improved transmission and detection of X-rays is achieved.

10 Claims, 6 Drawing Sheets

FLUORESCENT X-RAY ANALYZER WITH SEALED X-RAY SHIELD WALL

BACKGROUND OF THE INVENTION

1. Field of the Invention

The present invention relates to a fluorescent X-ray analyzer used, for example, in the investigation of unknown elements contained in a sample, such as their quantity and distribution state within the sample and, more particularly, to an improved fluorescent X-ray analyzer that can increase the effectiveness of the X-ray beam while improving the handling of samples.

2. Description of Related Art

In a fluorescent X-ray analyzer, as partially shown in FIGS. 6(A) and 6(B), a primary X-ray beam generated by an X-ray generator 61 is guided to an X-ray irradiation area 63 by means of an X-ray guide tube (XGT) 62, and the primary X-ray is emitted to a sample 67 on a sample stage 66 through an opening 65 formed in an X-ray shield wall 64 disposed in the X-ray irradiation area 63. The fluorescent X-ray generated at this time is detected by an X-ray detector 68. By using the XGT 62, in this arrangement, the primary X-ray can be reduced to a very small beam diameter, ranging from scores to hundreds of micrometers, and a very tiny X-ray irradiation portion of the sample 67 can be irradiated with a sufficiently large power, so that the tiny irradiation portion can be irradiated securely. In the diagram, reference numeral 69 is an optical microscope, 70 is a tank containing a medium for cooling the X-ray detector 68, and 71 is a signal amplifier.

When analyzing elements by using such a fluorescent X-ray analyzer, various methods are known, such as a method of measuring by keeping the X-ray irradiation area 63 having the sample stage 66 at atmospheric pressure, as shown in FIG. 6(A), and a method of measuring by enclosing the X-ray irradiation area 63 by having the sample stage 66 with a casing 72 isolated from the atmosphere, and evaluating the casing 72, or filling the casing 72 with helium gas (lie gas) which would absorb less primary X-rays or fluorescent X-rays than the atmosphere, as shown in FIG. 6(B).

However, when performing a fluorescent X-ray analysis in the atmosphere, as shown in FIG. 6(A), elements of lower fluorescent X-ray energy, such as Na, Mg, and Al, and elements lighter than Si, the fluorescent X-rays caused by irradiation of a primary X-ray to these elements suffer stronger effects of absorption in the atmosphere and, hence, these light elements are not detected if contained in the sample, or the intensity of the fluorescent X-ray is substantially lowered.

Alternatively, as shown in FIG. 6(B), when performing a fluorescent X-ray analysis in a vacuum or He gas, although there is no effect of absorption of the atmosphere, the casing 72 must be evacuated or purged with He gas every time the sample is replaced, and a considerably longer preparation time is required aside from the actual measurement. In this method, a living sample (such as a leaf of a tree) cannot be measured in a live state.

OBJECTS AND SUMMARY OF THE INVENTION

The invention is devised in the light of the above circumstances, and it is an object thereof to present a fluorescent X-ray analyzer capable of detecting even light elements, such as Na, Mg, and Al securely, without having to evacuate or purge with He gas every time the sample is replaced, while considerably decreasing the effects of absorption of the atmosphere.

To achieve the above object, the present invention provides a fluorescent X-ray analyzer characterized by leading a primary X-ray generated by an X-ray generator into an X-ray irradiation area by an X-ray guide tube, emitting the primary X-ray to a sample on a sample stage through a sealed opening formed in an X-ray shield wall disposed in the X-ray irradiation area, and detecting the fluorescent X-ray generated at this time by an X-ray detector, wherein a resin film of low X-ray absorption rate is stretched across the opening to sealingly divide into a first space comprising the X-ray guide tube and X-ray detector and a second space comprising the sample stage, the first space being set in a vacuum state.

Alternatively, the first space may be, instead of being placed in a state of vacuum, filled with He gas.

In this way, by stretching such a resin film having a low rate of X-ray absorption in the opening through which the primary X-ray or fluorescent X-ray passes, to divide into a first space comprising the X-ray guide robe and X-ray detector and a second space comprising the sample, stage, and evacuating the first space and subsequently filling the first space with He gas, the majority of the passage of primary X-ray and fluorescent X-ray is in the vacuum. As a result, absorption of primary X-ray or fluorescent X-ray by the atmosphere is significantly decreased, so that light elements, such as Na, Mg, and Al can be detected securely.

Since the sample stage on which the sample is positioned at the atmospheric pressure, it is not necessary to evacuate or purge with He gas every time a sample is replaced as needed in the prior art and, hence, a desired analysis can be done in a relatively short time period for added convenience.

BRIEF DESCRIPTION OF THE DRAWINGS

The objects and features of the present invention, which are believed to be novel, are set forth with particularity in the appended claims. The present invention, both as to its organization and manner of operation, together with further objects and advantages, may best be understood by reference to the following description, taken in connection with the accompanying drawings.

DETAILED DESCRIPTION OF THE PREFERRED EMBODIMENTS

The following description is provided to enable any person skilled in the art to make and use the invention and sets forth the best modes contemplated by the inventors of carrying out their invention. Various modifications, however, will remain readily apparent to those skilled in the art, since the generic principles of the present invention have been defined herein specifically to provide a fluorescent X-ray analyzer with an X-ray shield wall having a sealed aperture.

Figure 1:
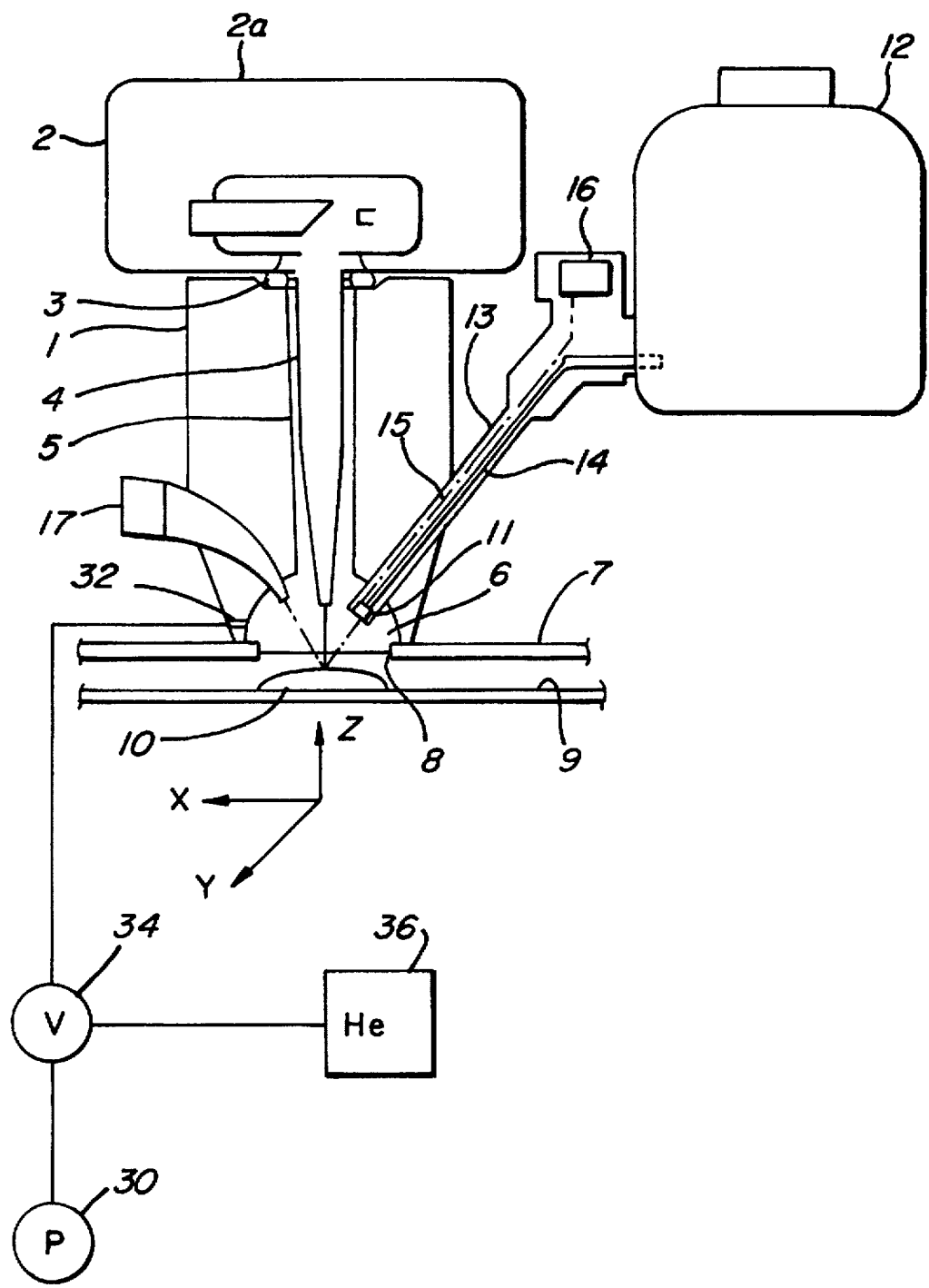
FIG. 1 is a block diagram of an example of a fluorescent X-ray analyzer of the present invention.
Figure 2:
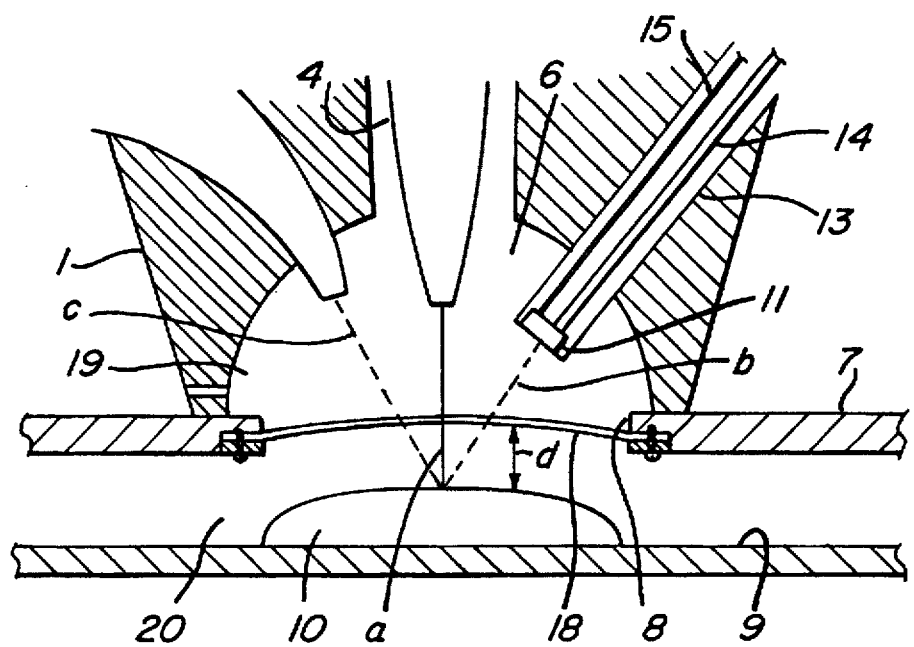
FIG. 2 is an essential magnified view of the fluorescent X-ray analyzer.

An embodiment of a fluorescent X-ray analyzer of the invention is shown in FIG. 1 and FIG. 2. In FIG. 1, reference numeral 1 denotes a main body block of the analyzer, and an X-ray generator 2 comprising an X-ray tube 2a and other components disposed thereabove. Reference numeral 3 is a seal unit interposed between the main body block 1 and X-ray generator 2. The main body block 1 has an insertion hole 5 for placing an XGT 4 for guiding the primary X-ray generated by the X-ray generator 2 and defining it into a proper beam diameter, and a lower space (X-ray irradiation area) 6 consecutive to the insertion hole 5 and opened downward.

Reference numeral 7 denotes an X-ray shield wall provided in the lower part of the main body block 1, more specifically below the lower end of the XGT 4, and an opening 8 of a proper size large enough to include the lower end of the XGT 4 is formed in this X-ray shield wall 7. Reference numeral 9 is a sample stage for supporting a sample 10 provided beneath the X-ray shield wall 7, and the sample stage 9 is designed to move linearly in the X, Y, Z directions by means of a drive mechanism not shown in the drawing.

Reference numeral 11 is an X-ray detector for detecting the fluorescent X-ray b (see FIG. 2) generated in the sample 10 when the sample 10 on the sample stage 9 is irradiated with a primary X-ray a (see FIG. 2), being composed of, for example, a semiconductor detector. The X-ray detector 11 is disposed at a lower end of a cold finger support 14 composed of a thermal conductive copper extending into a housing 13 consecutive to a tank 12 containing a cooling medium, such as liquid nitrogen, so as to confront the lower space 6. Reference numeral 15 is a signal pickup lead wire of the X-ray detector 11, and reference numeral 16 is a signal amplifier. Reference numeral 17 is an optical microscope, and c denotes a visible ray.

A pump 30 can evacuate the lower space 6 through a port 32 when valve 34 is activated. Subsequently, valve 34 can permit a source of helium 36 to fill the lower space 6.

Figure 6:
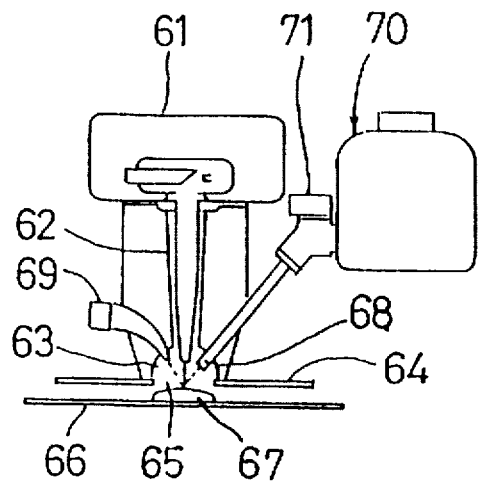
FIGS. 6(A) and 6(B) are diagrams showing the constitution of conventional fluorescent X-ray analyzers.
Figure 6:
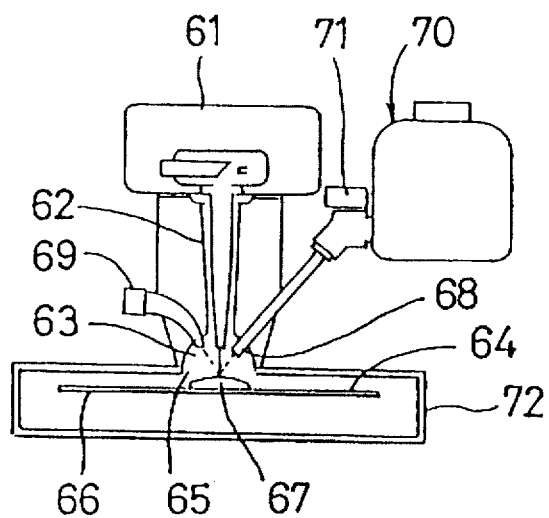

The same basic elements are provided as shown in the fluorescent X-ray analyzer of an atmospheric irradiation type shown in FIG. 6(A). The fluorescent X-ray analyzer of the present invention can be seen in more detail in the following points shown in FIG. 2.

That is, the diameter of the opening 8 formed in the X-ray shield wall 7 is, for example, 2 to 3 mm, and a thin resin film 18 is stretched in the opening 8 to divide the opening into a first space 19, comprising the XGT 4 and X-ray detector 11, and a second space 20, comprising the sample stage 9 and sample 10, and the first space 19 is arranged to be in a vacuum state.

Figure 7:
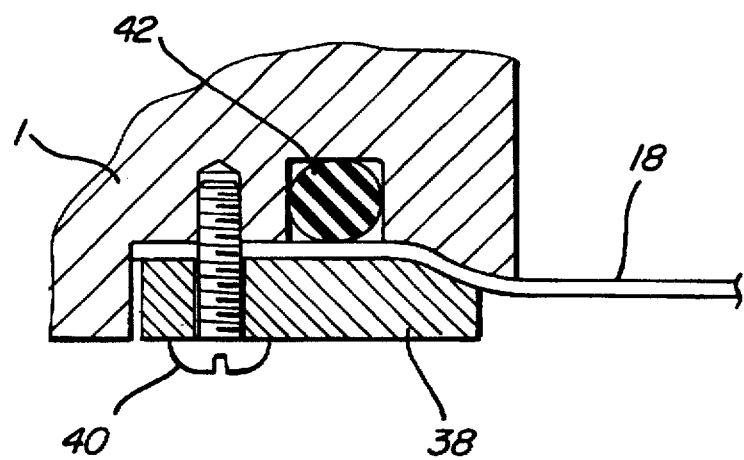
FIG. 7 is a partial cross-section of the sealing assembly.

FIG. 7 discloses a cross-sectional view of an annular mounting ring 38 that can be bolted to the body block 1 by bolts 40. An annular O-ring 42 can help seal the film 18.

The material of the resin film 18 is required to be transparent in order to see the position of the sample 10 on the stage 9 visually or by an optical microscope 17, and should be low in the absorption rate of X-rays, such as a primary X-ray a and fluorescent X-ray b. Additionally, the film 18 should not emit fluorescent X-rays as a result of an impact with the composition of the film itself, and should be strong enough to withstand a pressure equivalent to atmospheric pressure. As a film material to satisfy these conditions, for example, a polyethylene resin film is known, of which the thickness is preferably several micrometers.

As a degree of vacuum for the first space 19, for example, 1 Torr or less is desired, or more preferably approximately 0.1 Torr or less. The second space 20 is maintained at atmospheric pressure. The height of the sample stage 9 should preferably be adjusted so that the distance d between the resin film 18 and sample 10 may be 1 mm or less. By keeping the distance d as short as possible, the effect of absorption by the atmosphere can be minimized.

In a fluorescent X-ray analyzer of such a constitution, by stretching a resin film 18, of a low absorption rate of X-rays, in the opening 8 through which the primary X-ray a and fluorescent X-ray b pass, a first space 19, comprising the XGT 4 and X-ray detector 11 and a second space 20, comprising the sample stage 9 and sample 10, are provided. The first space 19 is maintained in a specific vacuum state and, hence, the absorption of the primary X-ray a and fluorescent X-ray b by the atmosphere is considerably decreased, thereby light elements, such as Na, Mg, and Al can be detected securely.

Moreover, since the sample stage for putting the sample on is at an atmospheric pressure, it is not necessary to evacuate or purge with He every time the sample is replaced, as needed in the prior art, and the desired analysis can be done in a short time period.

Figure 3:
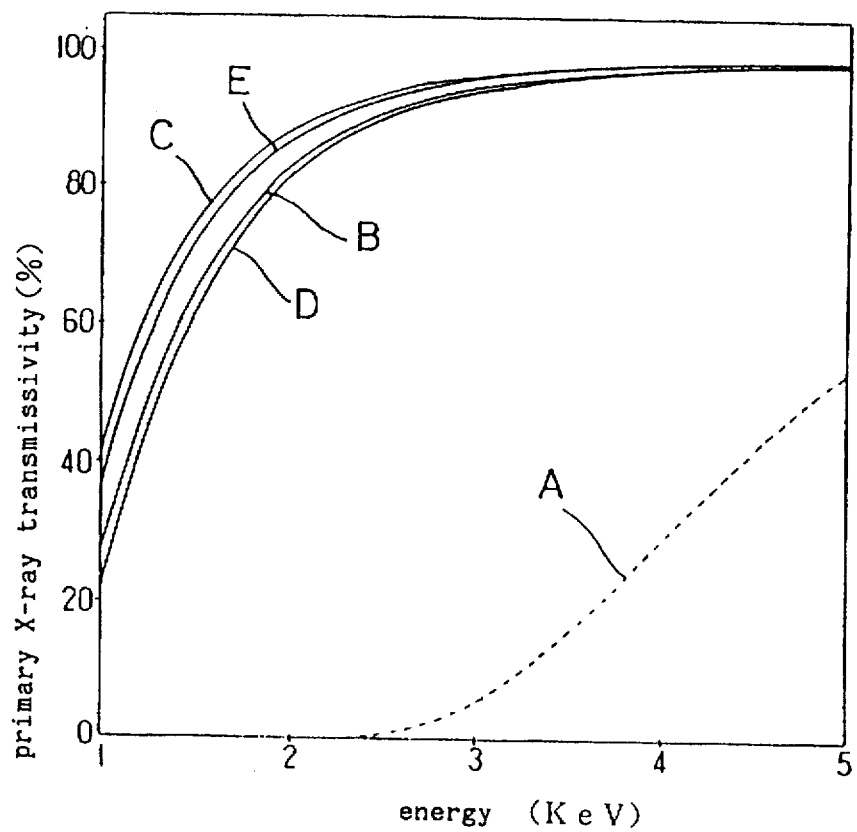
FIG. 3 is a diagram showing the relation of energy and primary X-ray transmissivity in the apparatus of the invention and in the conventional apparatus.
Figure 4:
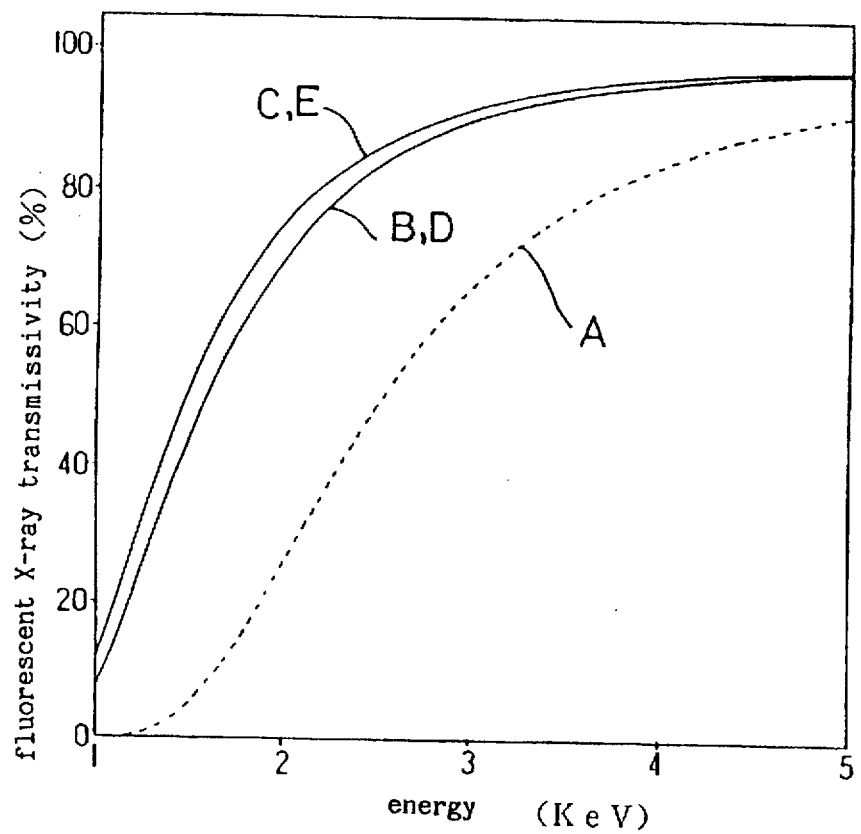
FIG. 4 is a diagram showing the relation of energy and fluorescent X-ray transmissivity in the apparatus of the invention and in the conventional apparatus.
Figure 5:
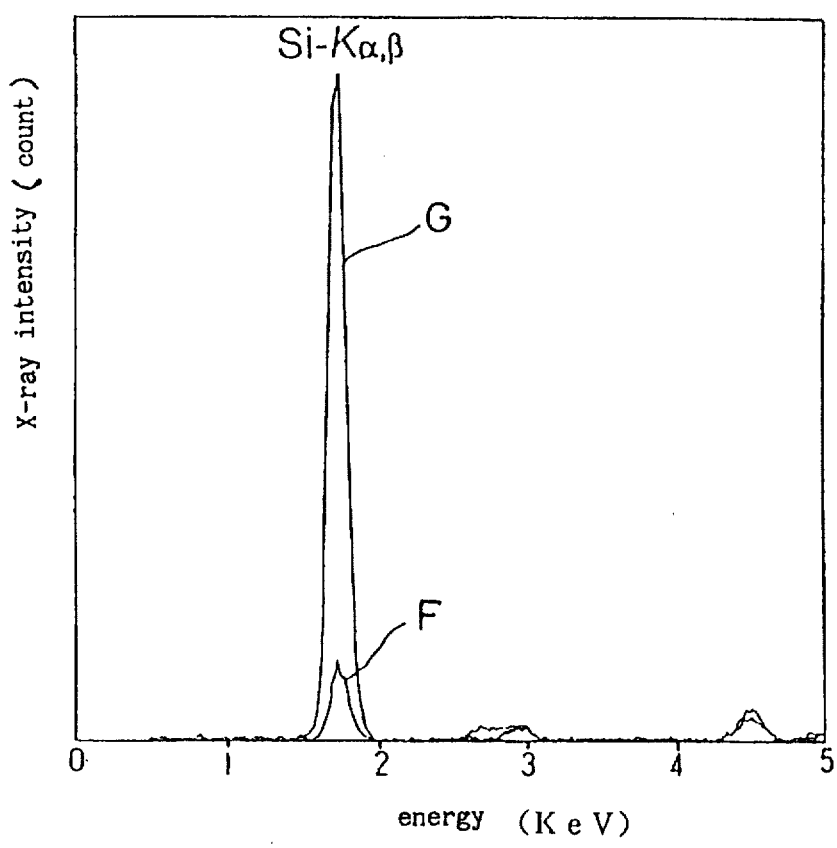
FIG. 5 is a diagram showing the relation of energy and X-ray intensity in the apparatus of the invention and in the conventional apparatus.

In this embodiment the first space 19 is set in a proper vacuum state, but, alternatively, the first space 19 may be purged with He gas, and the first space 19 may be filled with He gas which absorbs X-rays less than the atmosphere, so as to be equal to the atmospheric pressure. In such a constitution, if the resin film 18 cannot withstand the atmospheric pressure, it is still usable with a charge of He gas to balance the atmospheric pressure. In a sample analysis by using the fluorescent X-ray analyzer of the present invention and a conventional X-ray analyzer, and the test conditions were as follows:

FIGS. 3 to 5 show various data obtained in a sample analysis by using the fluorescent X-ray analyzer of the present invention and a conventional X-ray analyzer, and the test conditions were as follows:

A: Irradiation in the air, as shown in FIG. 6(A)

B: First space 19=vacuum, distance d=1 mm, resin film=4 µm thick as shown in FIGS. 1 and 2

C: First space 19=vacuum, distance d=1 mm, resin film=2 µm thick as shown in FIGS. 1 and 2

D: First space 19=He layer, distance d=1 mm, resin film=4 µm thick as shown in FIGS. 1 and 2

E: First space 19=He layer, distance d+1 mm, resin film=2 µm thick as shown in FIGS. 1 and 2

That is, the condition A is the conventional aerial measuring method, and the other conditions B to E conform to the irradiation method by the fluorescent X-ray analyzer of the present invention. The thickness of the resin film in the preferred embodiments can be approximately 2 µm to 4 µm thick.

First, FIG. 3 shows a relationship between the energy and primary X-ray a transmissivity when irradiated in the above conditions, and symbols A to E in the diagram correspond to the conditions A to E above. It is known from this diagram that the transmissivity of a primary X-ray is notably enhanced, as compared with the conventional aerial irradiation, event at low energy, in the fluorescent X-ray analyzer of the present invention.

FIG. 4 shows the relationship between the energy and fluorescent X-ray b transmissivity when irradiated in the above condition, and symbols A to E in the diagram correspond to the conditions A to E above. It is known from this diagram that the transmissivity of fluorescent X-ray b is notably enhanced, as compared with the conventional aerial irradiation, even at low energy, in the fluorescent X-ray analyzer of the present invention. It is also known that the transmissivity of the fluorescent X-ray b is not so different whether the first space 19 is a vacuum or filled with He gas.

FIG. 5 compares the intensity of a low energy fluorescent X-ray between the conventional measurement (measurement in the atmosphere) and the measurement by the fluorescent X-ray analyzer of the present invention, in which curve F relates to the prior art, and curve G represents the present invention, and it is known from FIG. 5 that the intensity of the low energy fluorescent X-ray is amplified about eight times in the present invention.

According to the present invention, as described herein, by sealingly stretching a resin film of a low absorption rate of X-rays across the opening formed in the X-ray shield wall provided in the X-ray irradiation area, to divide the opening into an upper first space comprising the XGT and X-ray detector and a second lower space comprising the sample stage, and evacuating the first space or filling the first space with He gas, the effects of the atmosphere can be reduced significantly and, hence, the transmissivity of the primary X-ray and the transmissivity of the fluorescent X-ray are notably enhanced, while the intensity of the low energy fluorescent X-ray is significantly amplified. Therefore, light elements such as Na, Mg, and Al which were hitherto impossible to detect by the conventional atmospheric measuring method can be easily detected.

Moreover, since the second lower space comprising the sample stage is at atmospheric pressure, it is not necessary to evacuate or purge with He gas every time a sample is replaced and, hence, the operation and measurement are made easier, and the total time required for measurement is shortened.

Also according to the invention, the intensity of soft X-ray of primary X-ray is increased, and the excitation efficiency is improved.

Those skilled in the art will appreciate that various adaptations and modifications of the just-described preferred embodiment can be configured without departing from the scope and spirit of the invention. Therefore, it is to be understood that, within the scope of the appended claims, the invention may be practiced other than as specifically described herein.

What is claimed is:

1. In a fluorescent X-ray analyzer characterized by leading a primary X-ray generated by an X-ray generator into an X-ray irradiation area by an X-ray guide tube, emitting the primary X-ray to a sample on a sample stage through an opening formed in an X-ray shield wall disposed in the X-ray irradiation area, and detecting the fluorescent X-ray generated with an X-ray detector, the improvement comprising:

a resin film of a low X-ray absorption rate sealingly stretched in the opening of the X-ray shield wall to divide the shield wall into a first space comprising the X-ray guide tube and X-ray detector and a second space comprising the sample stage; and means for placing the first space in an approximately vacuum state.

2. The invention of claim 1 wherein the resin film is approximately 2 μm to 4 μm thick.

3. The invention of claim 1 further including a mounting ring and seal member for securing the resin film.

4. The invention of claim 2 wherein the first space pressure is approximately 0.1 Torr.

5. In a fluorescent X-ray analyzer characterized by leading a primary X-ray generated by an X-ray generator into an X-ray irradiation area by an X-ray guide tube, emitting the primary X-ray to a sample on a sample stage through an opening formed in an X-ray shield wall disposed in the X-ray irradiation area, and detecting the fluorescent X-ray generated with an X-ray detector, the improvement comprising:

a resin film of a low X-ray absorption rate stretched in the opening of the X-ray shield wall to divide the shield wall into a first space comprising the X-ray guide tube and X-ray detector and a second space comprising the sample stage; and means for filling the first space with He gas.

6. An improved fluorescent X-ray analyzer comprising:

means for emitting an X-ray beam;

support means for supporting a sample to be irradiated by the X-ray beam;

an X-ray shield wall having an aperture transmissive to the X-ray beams and positioned adjacent to the support means, and a transparent film member extending across the aperture;

an X-ray detector positioned adjacent the support means and positioned on the same side of the X-ray shield wall as the means for emitting an X-ray beam; and means for evacuating the side of the X-ray shield wall containing the means for emitting an X-ray beam and the X-ray detector, whereby the transmission of X-rays is increased while the sample can be easily mounted on the support means.

7. The invention of claim 6 further including means for providing helium to the side of the X-ray shield wall adjacent the X-ray detector.

8. The invention of claim 7 wherein helium at atmospheric pressure is charged.

9. The invention of claim 6 wherein the film member is resin and approximately 2 μm to 4 μm thick.

10. The invention of claim 6 further including a mounting ring and seal member connected about the aperture for sealing the transparent film member.

* * * * *